(12) United States Patent
Pitulia

(10) Patent No.: US 7,409,070 B2
(45) Date of Patent: Aug. 5, 2008

(54) IMPLANT DEVICE

(75) Inventor: Dan Pitulia, Västra Frölunda (SE)

(73) Assignee: Entific Medical Systems AS, Göteborg (SE)

( * ) Notice: Subject to any disclaimer, the term of this patent is extended or adjusted under 35 U.S.C. 154(b) by 34 days.

(21) Appl. No.: 10/558,387

(22) PCT Filed: May 26, 2004

(86) PCT No.: PCT/SE2004/000818

§ 371 (c)(1),
(2), (4) Date: Nov. 29, 2005

(87) PCT Pub. No.: WO2004/105650

PCT Pub. Date: Dec. 9, 2004

(65) Prior Publication Data

US 2007/0009853 A1 Jan. 11, 2007

(30) Foreign Application Priority Data

May 30, 2003 (SE) .................................... 0301588

(51) Int. Cl.
H04R 25/00 (2006.01)

(52) U.S. Cl. ........................ 381/326; 381/324; 381/328; 381/329; 381/331; 606/73; 607/55; 607/137; 623/10; 600/386; 600/379

(58) Field of Classification Search .................. 607/55, 607/56, 57, 65, 103, 136, 137; 623/10; 600/372, 600/373, 375, 379, 383, 386, 559; 606/73; 381/60, 312, 322, 323, 324, 326, 328, 329, 381/331

See application file for complete search history.

(56) References Cited

U.S. PATENT DOCUMENTS 4,498,461 A 2/1985 Hakansson (Continued)

FOREIGN PATENT DOCUMENTS

WO WO 9612451 A1 5/1996

(Continued)

OTHER PUBLICATIONS

Entific Medical Systems AB; Baha Product Catalogue; 20 pages; Göteborg, Sweden (May 2002).

Primary Examiner—Wayne Young
Assistant Examiner—Dionne Pendleton
(74) Attorney, Agent, or Firm—Venable LLP; Eric J. Franklin

(57) ABSTRACT

An implant device for bone anchored hearing aids of the type that include a screw-shaped anchoring element for anchorage in the bone tissue, an abutment sleeve for skin penetration and arranged to be connected to the fixture with a screw connection and a tool for installing the implant into the bone tissue. The fixture and the abutment sleeve are made as a pre-mounted unit that unit is arranged to be installed in one step by means of the tool, which is arranged to cooperate with a tool engaging portion on the abutment sleeve. This arrangement requires fewer pieces to handle for the surgeon during the installation, which means that the surgical procedure can be carried out in a simpler and predetermined way, at the same time as the advantages inherent in a two-piece implant device are maintained.

11 Claims, 3 Drawing Sheets

U.S. PATENT DOCUMENTS

| | | | |
|---|---|---|---|
| 4,712,681 A * | 12/1987 | Branemark et al. | 206/438 |
| D294,295 S | 2/1988 | Branemark | |
| 5,735,790 A * | 4/1998 | Håkansson et al. | 600/25 |
| 5,951,601 A | 9/1999 | Lesinski et al. | |
| 5,987,344 A * | 11/1999 | West | 600/373 |
| 6,053,920 A * | 4/2000 | Carlsson et al. | 606/72 |
| 6,599,297 B1 * | 7/2003 | Carlsson et al. | 606/109 |
| 6,628,991 B2 * | 9/2003 | Kuzma et al. | 607/137 |
| 6,802,839 B2 * | 10/2004 | Behl | 606/32 |
| 6,840,919 B1 * | 1/2005 | Håkansson | 604/175 |
| 2003/0176866 A1 | 9/2003 | Westerkull | |

FOREIGN PATENT DOCUMENTS

| | | |
|---|---|---|
| WO | WO 9855049 A1 | 12/1998 |
| WO | WO 0209622 A1 | 2/2002 |

* cited by examiner

IMPLANT DEVICE

CROSS-REFERENCE TO RELATED APPLICATIONS

This application claims priority under 35 USC § 119 to Swedish patent application no. 0301753-0 filed on 13 Jun. 2003 and is the national phase application of PCT/SE2004/000834 under 35 U.S.C. § 371.

FIELD OF THE INVENTION

The present invention relates to an implant device for bone anchored hearing aids. The device comprises a screw-shaped anchoring element (fixture) for permanent anchorage in the bone tissue, an abutment sleeve for skin penetration arranged to be connected to the fixture by means of a screw connection and a tool for installing the implant in the bone tissue. The invention is specifically intended to be used in connection with hearing aid devices of the bone conduction type, i e hearing aid devices by which the sound is transmitted mechanically via the skull bone directly to the inner ear of a person with impaired hearing. However, the invention is not limited to this specific application, but can be used in connection with other types of hearing aid devices for anchorage in the skull bone.

BACKGROUND OF THE INVENTION

For persons who cannot benefit from traditional, air conduction hearing aids there are other types of sound transmitting hearing aids on the market, ie bone anchored hearing aids which mechanically transmit the sound information to a persons inner ear via the skull bone by means of a vibrator. The hearing aid device is connected to an anchoring element in the form of an implanted titanium screw installed in the bone behind the external ear and the sound is transmitted via the skull bone to the cochlea (inner ear), ie the hearing aid works irrespective of a disease in the middle ear or not. The bone anchoring principle means that the skin is penetrated which makes the vibratory transmission very efficient.

This type of hearing aid device has been a revolution for the rehabilitation of patients with certain types of impaired hearing. It is very convenient for the patient and almost invisible with normal hair styles. It can easily be connected to the implanted titanium fixture by means of a bayonet coupling or a snap in coupling. One example of this type of hearing aid device is described in U.S. Pat. No. 4,498,461 and it is also referred to the BAHA® bone anchored hearing aid marketed by Entific Medical Systems in Göteborg.

The fixtures which are used today for the bone anchored hearing aid devices are normally designed in such a way that a screw tap is required to form an internal thread in the hole drilled in the skull bone before the screw is inserted. One example of such a fixture is illustrated in U.S. Pat. No. Des. 294,295. This fixture has an external thread with small cutting edges which have a scraping effect in the pre-tapped bone hole. The fixture has also a flange which functions as a stop against the bone surface when the fixture is screwed down into the skull bone. The flange is also in this case provided with through holes for bone ingrowth or the like.

However, it is also previously known to use self-tapping fixtures for the hearing aids. The advantage with that type of fixtures is that they can be inserted without the use of any screw tap, see SE 0002627-8. The installation of the implant is then much easier as at least one tool and one step in the installation procedure of the implant is eliminated.

The implants which are used on the market today are normally in two pieces, one piece consists of the screw-shaped anchoring element (fixture) and the other piece consists of the abutment sleeve for skin penetration. The reason for this two-piece design is the fact that the surgical technique which normally has been used for installing the implants has been carried out as a two-step procedure. In the first step the fixture is inserted and maintained unloaded during a healing period of some months or so. After this healing period the second step of the surgical procedure, ie the connection of the abutment sleeve by means of a screw connection, is carried out.

Thanks to this two-part design the implants can be upgraded if necessary without removing the fixture, and if the abutment sleeve is damaged then it can also be replaced without need of removal of the bone anchored screw.

The disadvantage with these two-part implants is the fact that the number of individual pieces to handle is increased and thereby the surgery time. Normally the fixture is installed by means of a so-called fixture mount which is attached to the fixture by means of a screw joint and the fixture mount has to be removed after the fixture has been inserted. After this moment the abutment sleeve has to be attached in correct position to the fixture by means of a very small screw, either directly after the insertion of the fixture or after a suitable healing period. In both cases there is a risk that the abutment sleeve is attached to the fixture with a too small tightening torque (then there is a risk that the screw joint is loosening) or a too big tightening torque (then there is a risk that the anchorage of the fixture screw in the bone is jeopardized).

By SE 9702164-6 it is previously known to integrate a flange fixture with a first coupling part so that an integral one-piece member is formed. The disadvantage with such an integral implant is the fact that a deformation zone has to be arranged between the flange fixture part and the coupling part of the implant. This deformation zone has at the same time the function of a dismounting zone within which the first coupling part can be separated from the implant by means of a specific tool (cylindric cutter) if a dismounting of the main parts of the implant should be necessary. In order to be able to re-connect the parts with each other it is necessary to provide a washer to bridge the milled away portion of the implant. The simplified installation procedure with such an implant is then counteracted by the complicated procedure which is required if a dismounting should be necessary.

SUMMARY OF THE INVENTION

One object of the present invention is to provide an implant device of the above-mentioned type which gives the surgeon a less number of pieces to handle during the installation which means that the surgical procedure can be carried out in a more simple way. However, the implant device should at the same time be designed in such a way that the advantages inherent in a two-piece implant device shall be maintained.

A further object of the invention is to provide an implant device in which the risk for a mistake in the surgical procedure, for instance an incorrect mounting of the fixture mount or the abutment sleeve, an incorrect tightening torque or the like, is reduced.

The invention is mainly characterized in that the fixture and the abutment sleeve are made as a pre-mounted unit which unit is arranged to be installed in one step by means of a tool which is arranged to cooperate with a tool engaging portion on the abutment sleeve.

According to a preferred embodiment the fixture is a self-tapping fixture.

According to a further preferred embodiment the tool comprises a first connecting part for machine insertion of the implant unit as well as a second connecting part for manual insertion of the implant device.

BRIEF DESCRIPTION OF THE DRAWINGS

In the following the invention will be described more in detail with reference to the accompanying drawings, in which.

DETAILED DESCRIPTION OF EMBODIMENTS OF THE INVENTION

Figure 1:
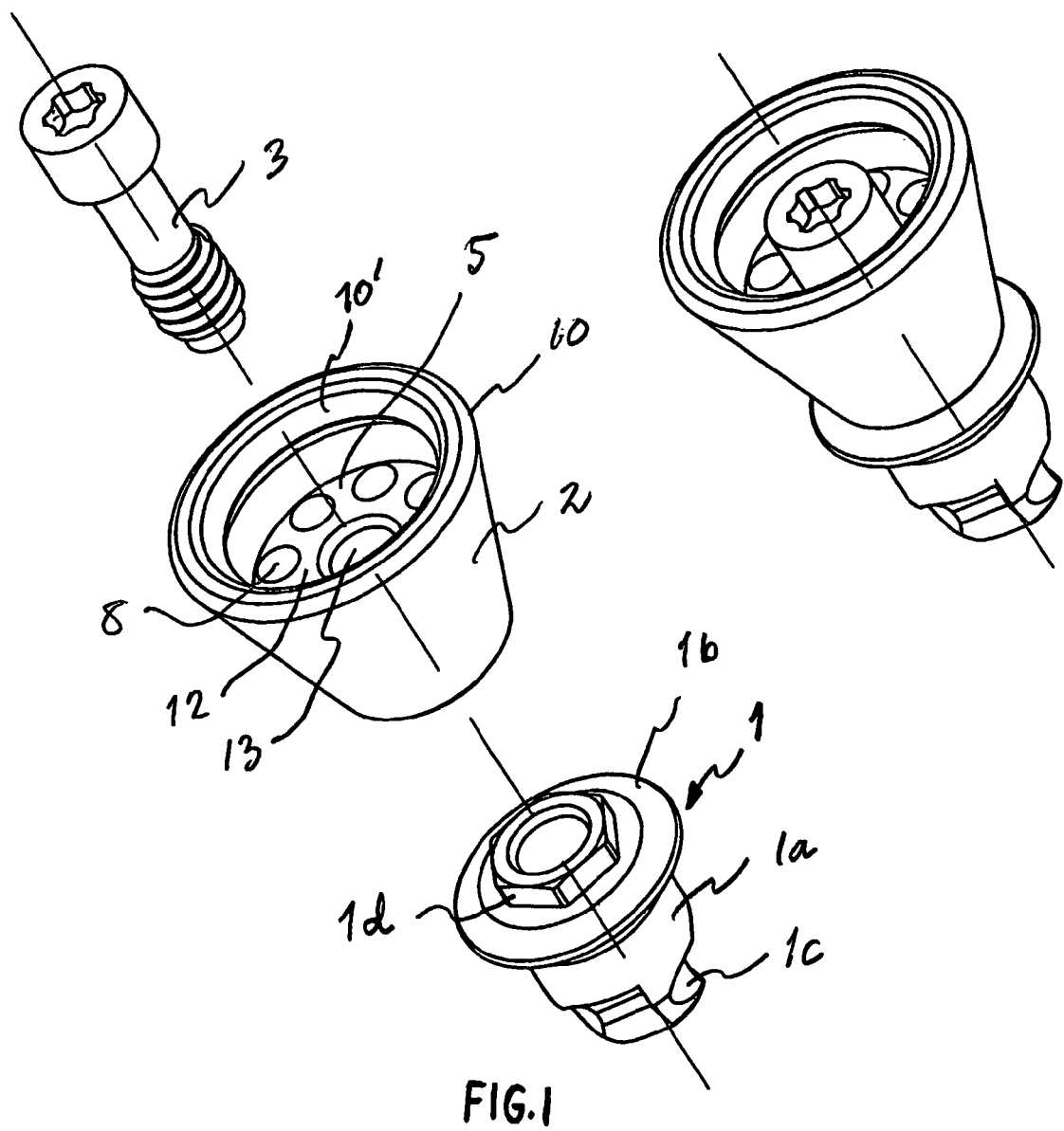
FIG. 1 illustrates the main parts of an implant device according to the invention, separated as well as pre-mounted.

FIG. 1 illustrates a screw-shaped anchoring element, a so-called fixture 1. The fixture is made of titanium which has a known ability to integrate with the surrounding bone tissue, so-called osseointegration. The fixture has a threaded part 1a which is intended to be installed into the skull bone and a flange 1b which functions as a stop when the fixture is installed into the skull bone. The apical part of the fixture has a known tapping ability with in this case three self-tapping edges 1c. A fixture of this type is described in the above-mentioned SE 0002627-8 and will therefore not be described in any detail here.

Figure 2:
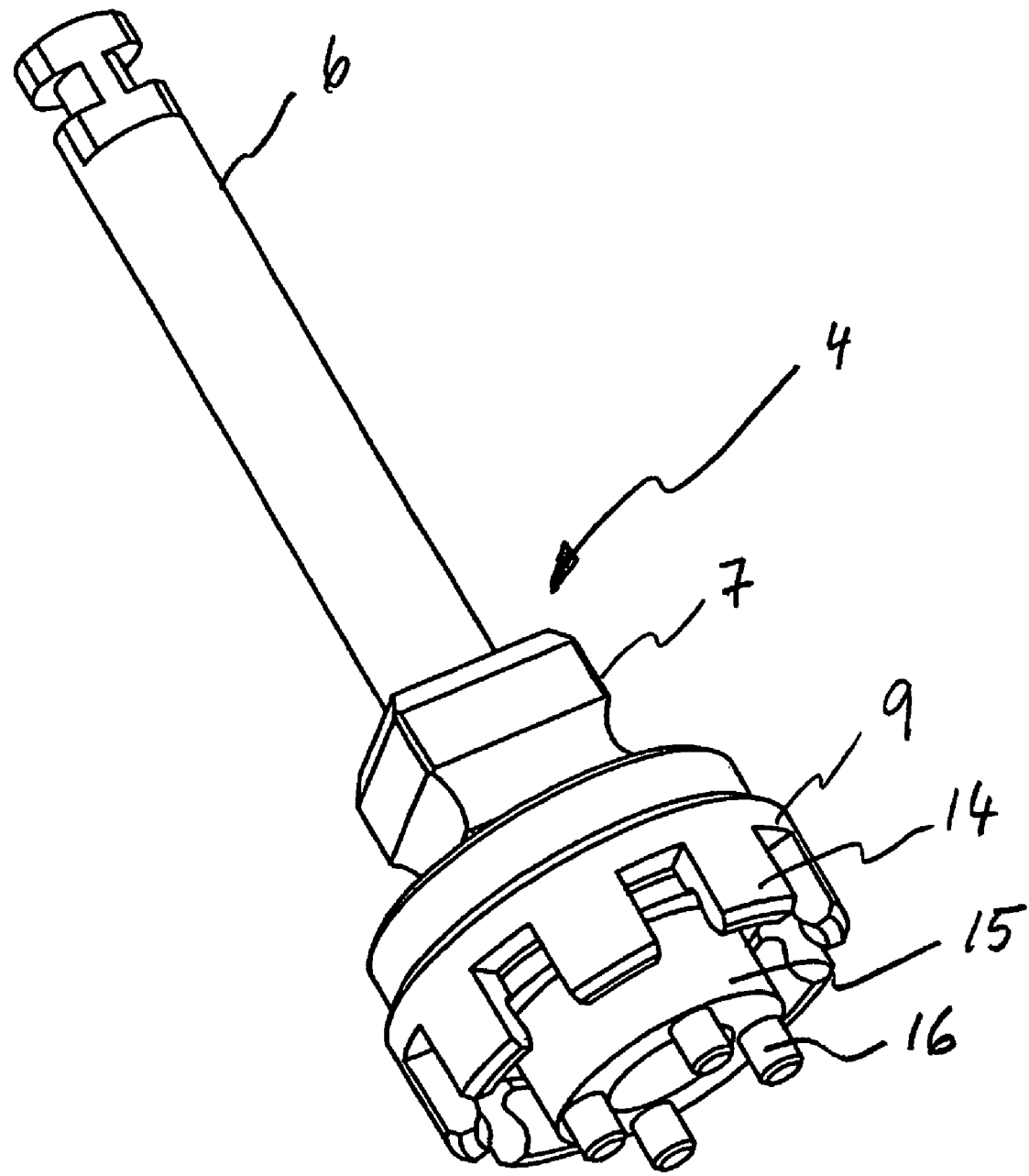
FIG. 2 illustrates a tool for installation of the pre-mounted implant device.

The skin penetrating part of the implant comprises a conical abutment sleeve 2 which is also previously known per se as a separate component. The abutment sleeve is provided with an inner annular flange 10' at its upper edge 10 in order to cooperate with a second coupling part (not shown) by means of snap-in action. The abutment sleeve has an internal shoulder 12 with a central opening 13 for the screw 3 and a number of peripherically arranged through holes or recesses 8 which function will be described more in detail in connection with the tool in FIG. 2.

According to the invention the three main parts are delivered in the form of a pre-mounted device as illustrated in FIG. 1. This means that the implant device is delivered pre-mounted in its package to the surgeon who is then installing the entire device in one step. The abutment sleeve is pre-mounted to the fixture at the manufacturing site with the correct tightening torque and the surgeon does not need to know the correct tightening torque or handle the separate pieces.

In contrast to the previously known implants the fixture hex 1d is not used for tool engagement during insertion, but instead the recesses 8 in the abutment sleeve are used. These recesses are located on the upper part of the implant device and more visible than the hex which was previously used for the tool engagement and then required the use of a specific fixture mount for the installation.

Previously a screw-driver and a counter torque device has been used for mounting the abutment sleeve on the fixture. According to the present invention only one tool 4 is used, see FIG. 2. The tool comprises a first connecting part 6 for a conventional dental drilling machine as well as a second connecting part in the form of a rectangular portion for manual insertion of the implant. The base portion of the tool comprises a resilient ring 9 with a number of stubs 14 for cooperation with the edge 10 of the abutment sleeve for providing a lifting function for the tool.

The tool is also provided with a lower, central protruding portion 15 with a number of peripherally located, in the longitudinal direction extending spikes 16 which spikes during insertion of the implant unit, are arranged to cooperate with said holes or recesses 8 on the abutment sleeve in order to screw down the implant unit in the bone tissue into a desired position.

The tool is preferably made of stainless steel while the resilient ring 9 can be made of a plastic material.

Figure 3:
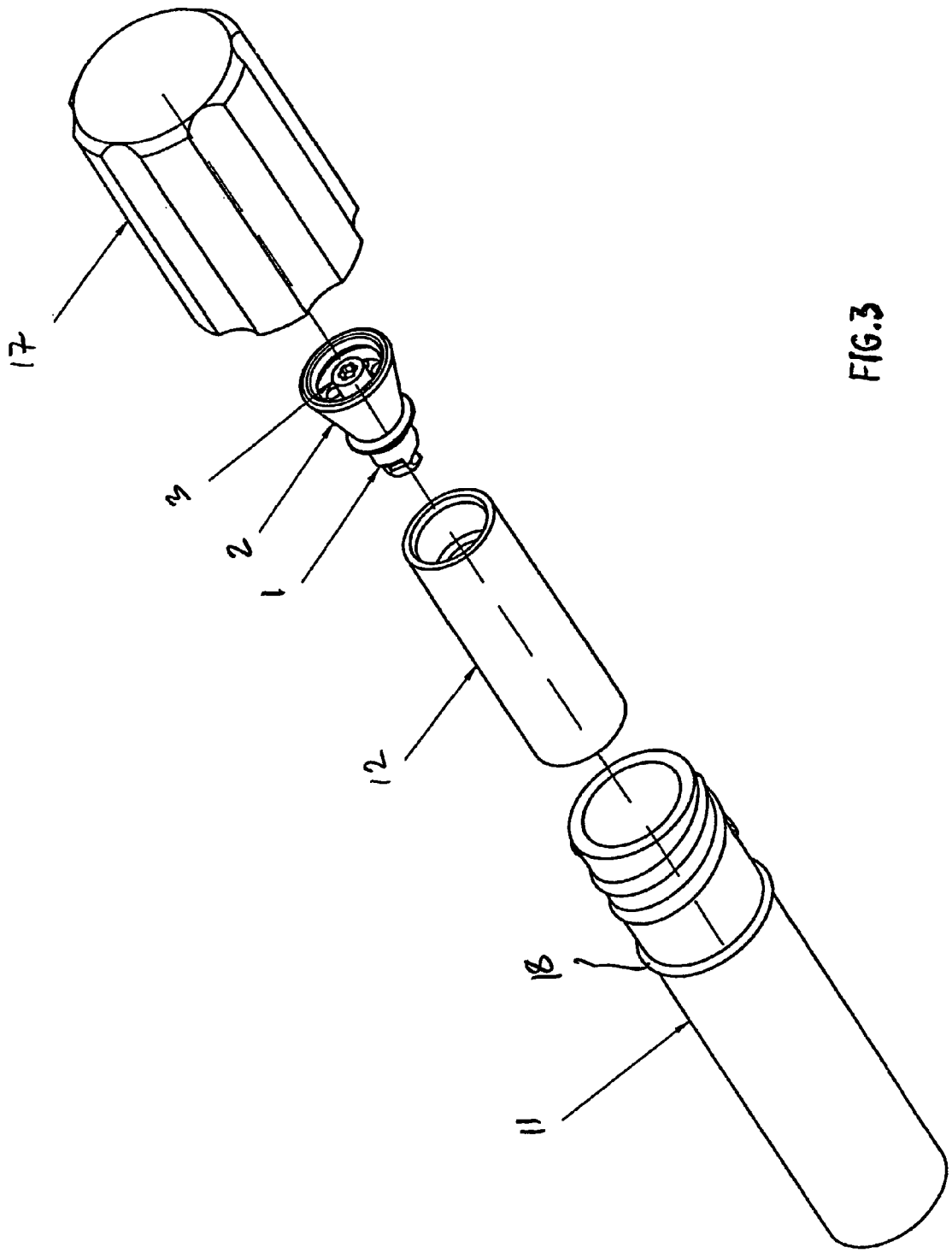
FIG. 3 illustrates a package for the pre-mounted implant device.

The pre-mounted implant device is delivered sterile in a plastic package 11 comprising a titanium packaging sleeve 12 in order to retain the implant device in a predetermined position in the plastic package, see FIG. 3. At the surgery the plastic package is broken by removing the plastic lid 17 and the pre-mounted implant device is then separated from the titanium packaging sleeve 12 by means of the tool 4 and the lifting function.

By placing the pre-mounted implant device in a titanium packaging sleeve 12 it is protected so that the tool will not come into contact with the fixture part when the implant device is removed from the packaging. A sealing ring 18 is arranged on the cylindrical outer surface of the plastic package to provide a tightening between the plastic package and the lid 17. The sealing ring 18 can be adjusted in the longitudinal direction to provide a tightening even for different positions of the plastic lid 17 on the package.

The invention is not limited to the embodiment which is illustrated in the drawings but can be varied within the scope of the accompanying patent claims.

The invention claimed is:

1. An implant device for a bone anchored hearing aid, comprising:
    a pre-mounted unit comprising a screw-shaped anchoring fixture configured to be anchored in bone tissue;
    an abutment sleeve configured to penetrate skin and comprising a tool engaging portion, and a screw connecting the abutment sleeve to the fixture, wherein the tool engaging portion of the abutment sleeve comprises a plurality of symmetrically arranged recesses or holes; and
    a tool configured to install the entire pre-mounted unit into the bone tissue in one step, wherein the tool is configured to cooperate with the tool engaging portion of the abutment sleeve when installing the implant into the bone tissue, and wherein the tool comprises a plurality of spikes configured to cooperate with the recesses or holes in the abutment sleeve during installation and tightening of the implant unit.

2. The implant device according to claim 1, wherein the fixture comprises self-tapping edges and a flange operative as a stop when the fixture is installed in the bone tissue.

3. The implant device according to claim 1, wherein the tool comprises a first connecting part adapted to engage a machine driver to install the implant device and a second connecting part for manual insertion of the implant device.

4. The implant device according to claim 1, wherein the tool comprises a resilient ring configured to cooperate with an edge of the abutment sleeve to provide a lifting function.

5. The implant device according to claim 4, further comprising:
    a sterile package configured to contain the implant device; and
    a titanium packaging sleeve configured to retain the implant device in a predetermined position in the sterile package, wherein after opening the sterile package the implant device is configured to be separated from the titanium packaging sleeve with the tool and the lifting function.

6. The implant device according to claim 5, wherein the sterile package comprises a package portion and a lid portion, the package portion comprising a sealing ring configured to provide a tightening between the package portion and the lid portion.

7. The implant device according to claim 6, wherein the sterile.

8. The implant device according to claim 6, wherein the sterile package comprises a cylindrical outer surface.

9. The implant device according to claim 6, wherein the sealing ring is arranged on an outer surface of the sterile package.

10. The implant device according to claim 6, wherein the package portion and lid portion comprise a screw connection.

11. The implant device according to claim 6, wherein the sealing ring is adjustable in a longitudinal direction to provide tightening for different positions of the lid portion on the package portion.

* * * * *